United States Patent [19]

Soula et al.

[11] Patent Number: 5,214,176

[45] Date of Patent: May 25, 1993

[54] ORGANOSILICON COMPOUNDS

[75] Inventors: Gerard Soula, Meyzieu; Gerard Mignani, Lyons, both of France

[73] Assignee: Rhone-Poulenc Chimie, Courbevoie, France

[21] Appl. No.: 340,778

[22] Filed: Apr. 20, 1989

[30] Foreign Application Priority Data

Apr. 20, 1988 [FR] France .................. 88 05214

[51] Int. Cl.$^5$ .................. C07F 7/08; C07F 7/10
[52] U.S. Cl. .................. 556/404; 556/413; 556/415; 556/422; 556/430; 546/14; 548/406; 549/4
[58] Field of Search .......... 556/415, 413, 430, 404, 556/422; 546/14; 548/406; 549/4

[56] References Cited

U.S. PATENT DOCUMENTS 2,429,883  10/1947  Johannson .................. 556/410

OTHER PUBLICATIONS

Bozant et al., "Organosilicon Compounds", vol. 2, Part 1, Academic Press, N.Y. (1965), pp. 472, 522, and 559.

*Primary Examiner*—Paul F. Shaver
*Attorney, Agent, or Firm*—Burns, Doane, Swecker & Mathis

[57] ABSTRACT

Novel organosilicon compounds having a second order hyperpolarizability coefficient $\beta$ greater than zero, well suited for use in the field of nonlinear optics, e.g., in telecommunication devices, have the general formula:

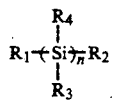

which n is an integer ranging from 1 to 20; $R_1$ is an electron donating group; $R_2$ is an electron accepting group; $R_3$ is an alkyl radical having from 1 to 8 carbon atoms, a hydrogen atom, an aryl radical, or an $R_1$ or $R_2$ radical; and $R_4$ is an alkyl radical having from 1 to 8 carbon atoms, a hydrogen atom, an aryl radical, or an $R_1$ radical when $R_3$ is not an $R_2$ radical or an $R_2$ radical when $R_3$ is not an $R_1$ radical.

9 Claims, No Drawings

ORGANOSILICON COMPOUNDS

BACKGROUND OF THE INVENTION

1. Field of the Invention

The present invention relates to novel organosilicon compounds, to a process for the preparation thereof, and to their applications in the field of nonlinear optics.

This invention especially relates to novel hyperpolarizable organosilicon compounds which are particularly active in nonlinear optics applications.

2. Description of the Prior Art

As reported by J. Zyss and I. Ledoux in the article in *L'Echo des Recherches*, 1st quarter, 1987, entitled "Organic molecules and the treatment of optical signals", the development of optical telecommunications requires the availability of components that include materials having strong nonlinear capabilities of the second or third order.

Numerous compounds, both organic and inorganic, are thus used in different forms, such as solutions, polymers, doped polymers, monomolecular layers, liquid crystals, single crystals, polymeric liquid crystals, and the like.

The organic compounds are especially interesting, as the synthesis of a wide variety of products is generally possible. Furthermore, most of the organic compounds have a great resistance to external effects (humidity, acidity, oxidation, etc.).

J. F. Nicoud and R. J. Twieg, in their paper entitled "Design and synthesis of organic compounds for efficient second harmonic generation" list different molecules which are active in the field of nonlinear optics.

These molecules have carbon chain skeletons generally comprising aromatic rings, substituted on the one hand by electron donating groups and, on the other, by electron accepting groups.

Thus, the dislocation and circulation of $\pi$ electrons and the non-centrosymmetry of the molecule generate a strong hyperpolarizability of the second and third order.

Large scale research efforts have to date been continuously carried out in an effort to develop novel compounds having nonlinear optical activity.

SUMMARY OF THE INVENTION

Accordingly, a major object of the present invention is the provision of a novel class of organometallic compounds, and, more particularly, a novel class of organosilicon compounds, displaying hyperpolarizability.

Briefly, the present invention features novel organosilicon compounds having the following general formula:

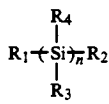

in which n is an integer ranging from 1 to 20; $R_1$ is an electron donating group; $R_2$ is an electron accepting group; $R_3$ is an alkyl radical having from 1 to 8 carbon atoms, a hydrogen atom, an aryl radical, or an $R_1$ or $R_2$ radical; and $R_4$ is an alkyl radical having from 1 to 8 carbon atoms, a hydrogen atom, an aryl radical, an $R_1$ radical when $R_3$ is not an $R_2$ radical, or an $R_2$ radical when $R_3$ is not an $R_1$ radical.

DETAILED DESCRIPTION OF THE PREFERRED EMBODIMENTS OF THE INVENTION

More particularly according to the present invention, the $R_1$ electron donating group advantageously has the following general formula:

in which $R_5$ is an arylene radical; and the radicals D, which may be identical or different, are each a hydrogen atom or an electron donating radical selected from among amino, alkylamino, dialkylamino, arylamino, hydroxyl, thiolo, alkylthio, arylthio, alkoxy, aryloxy, alkyl halide, oxy,

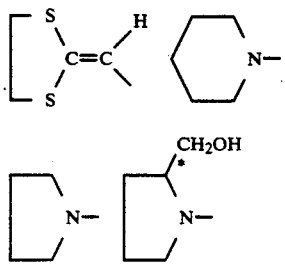

and m is an integer equal to 1, 2 or 3.

D is not a hydrogen atom if $R_2$ is an aryl radical that is not substituted by one or more electron attracting groups.

The preferred $R_1$ radials according to the invention are:

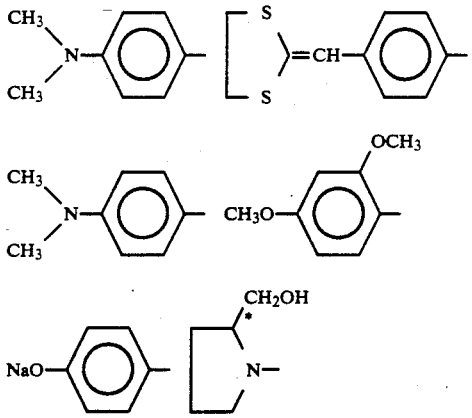

In a preferred embodiment of the invention, the $R_2$ electron accepting group has the following general formula:

in which $R_6$ is an arylene radical; p is an integer equal to 1, 2 or 3; and the radicals A, which may be identical or different, are each a hydrogen atom or an electron accepting radical selected from among halogeno, nitro, cyano, nitroso, quaternary ammonium, pyridinyloxy, $CF_3$, alkyl quaternary ammonium, acyl, alkoxysulfonyl, aryloxysulfonyl radicals, or radicals of the following formulae:

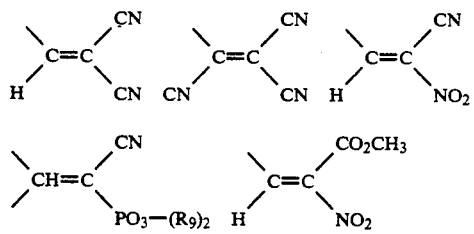

wherein $R_9$ is an alkyl radical having from 1 to 6 carbon atoms or an aryl radical, with the proviso that A is not a hydrogen atom when $R_1$ is an aryl radical that is not substituted by one or more electron donating groups.

The preferred $R_2$ radicals according to the invention are:

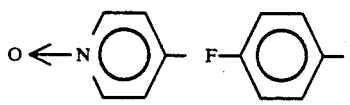

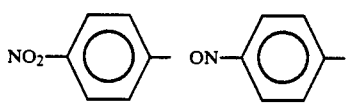

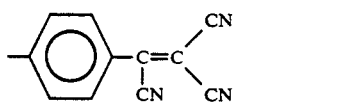

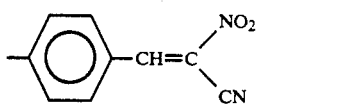

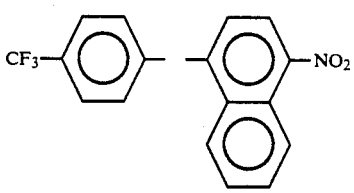

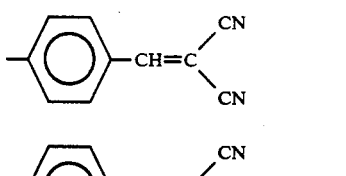

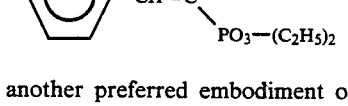

In another preferred embodiment of the invention, the $R_3$ and $R_4$ radicals, which may be identical or different, are each methyl, ethyl, propyl or phenyl radicals, or an $R_1$ or $R_2$ radical as defined above.

Thus, exemplary compounds of the invention are those having the following structural formulae:

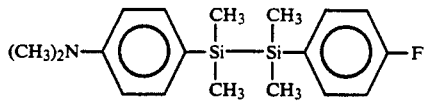

-continued

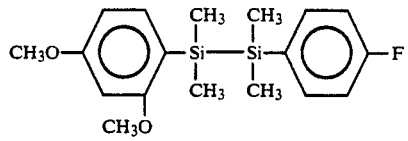

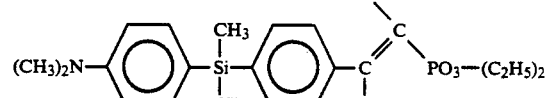

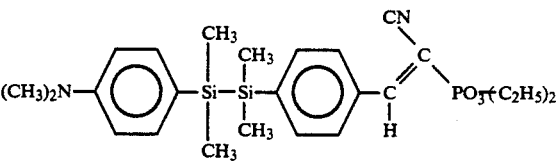

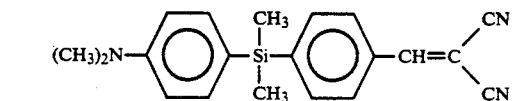

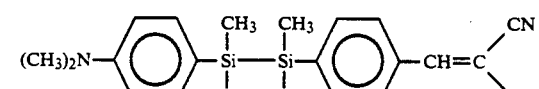

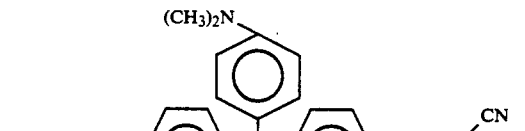

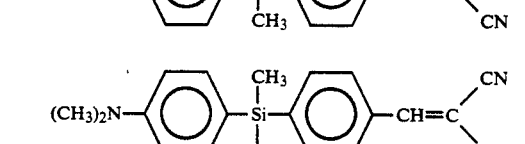

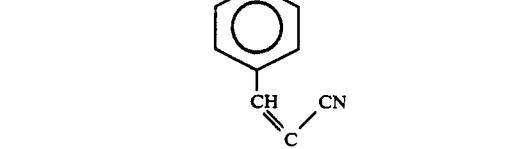

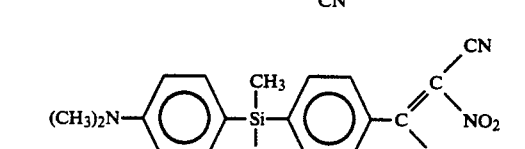

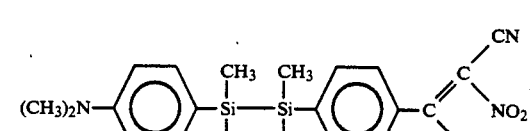

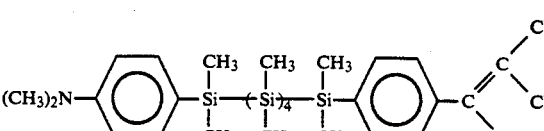

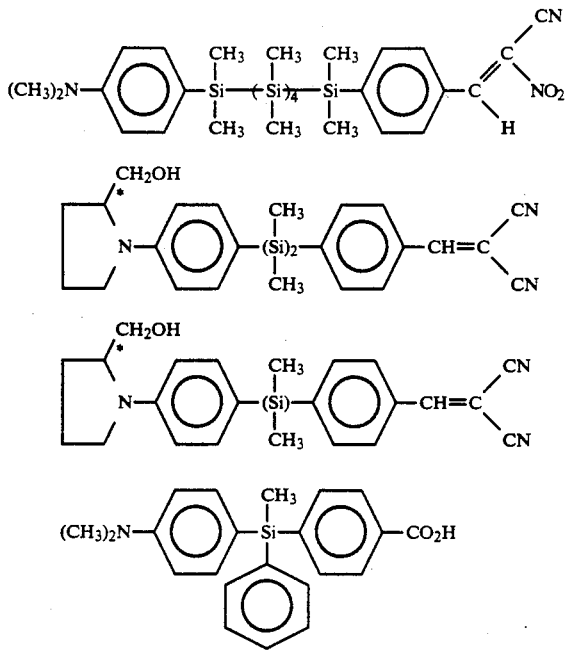

These compounds may be prepared using general techniques for the synthesis of organosilicon compounds. Thus, the most typically used such process is the synthesis employing organometallic compounds, and in particular, organomagnesium compounds.

In general, the synthesis of the compounds of the invention is carried out by reacting an organomagnesium compound containing a radical $R_1$ with a halosilane of the formula:

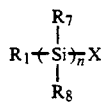

in which X is a halogen atom; and $R_7$ and $R_8$, which may be identical or different, are each an $R_1$, $R_2$, $R_3$ or $R_4$ radical, or a halogen atom (with $R_1$, $R_2$, $R_3$ and $R_4$ being as above defined). Preferably, the halosilane is an organohalosilane containing either the radical $R_4$, or the radical $R_3$, or both such radicals. The resulting compound is then reacted with a second organomagnesium compound containing an $R_2$ radical.

Obviously, the order of the reactions with the organomagnesium compounds may be reversed.

Furthermore, it is also possible to use as the organometallics, organomagnesium compounds containing one or more radicals related to $R_1$ or $R_2$, hereinafter designated as the radicals $R_{10}$. In this embodiment, the organosilicon compound produced is subjected to one or more reactions to the aforementioned $R_{10}$ radical which is similar to the radicals $R_1$ or $R_2$, to provide the definite formula of the organosilicon compound. It is possible in this manner, for example, to subject the organosilicon compound to such reactions as hydrolysis, amminolysis, carboxylation, carbonylation, reaction with compounds having an active methylene group (KNOEVENAGEL reaction), and the like.

The compounds of the invention have the important property of being active in nonlinear optics and, thus, are suitable for use in devices for the treatment of waves, particularly in the field of long distance telecommunications.

Indeed, the activity of such materials in nonlinear optics is determined by the $\beta$ and $\gamma$ coefficients of hyperpolarizability of the second, third or n order.

The hyperpolarizability of a compound is directly related to the molecular dipole moment by the fundamental relationship:

$$\mu = \mu^o + \alpha + E + \beta E.E + \gamma E.E.E + \ldots$$

in which $\mu$ and $\mu^o$ represent the dipolar moments, electromagnetic field.

E represents the electric or magnetic field of excitation.

$\alpha$, $\beta$ and $\gamma$ represent the coefficients of polarizability and hyperpolarizability.

In effect, the coefficient $\alpha$ is the coefficient of polarizability of the molecule and reflects its activity in linear optics.

The coefficients $\beta$ and $\gamma$ represents the hyperpolarizability, respectively, of the second and third order.

These coefficients reflect the aharmonicity of the electrical potential in the molecule and is strongly dependent on its symmetry.

Furthermore, the coefficients of odd order, such as the coefficient $\gamma$, are never zero for all of the molecules. In contrast, the coefficients of even order, such as the coefficient $\beta$, are zero for symmetrical or centrosymmetrical molecules. It is advantageous to use molecules with a non-zero $\beta$ coefficient in nonlinear optical applications, such as, for example, electrooptical devices, electrooptical modulators, parametric amplifiers, frequency doubling devices, etc.

To determine and measure the $\beta$ coefficient of molecules, it is compared with that of a reference molecule, i.e., urea.

The molecular hyperpolarizability coefficient $\beta$ of a compound is generally measured in a solvent medium, such as, for example, acetone, water, or dimethylsulfoxide, by the method known as the EFISH technique, briefly described hereinbelow.

The liquid solution containing a number N of molecules by cubic cm is polarized by an electrical field $E^o$.

The polar molecules are oriented in the electrical field.

An optical field $E^\omega$ passes through the solution, which radiates a $2\omega$ harmonic wave according to the relationship:

$$P^{2\omega} N \cdot (\gamma - \beta\mu) E^o (E^\omega)^2$$

wherein $P^{2\omega}$ represents the polarization for the second harmonic;

$\alpha$ represents the cubic hyperpolarizability coefficient and is negligible;

$\mu$ represents the dipolar moment of the molecule.

The measurement of $P^{2\omega}$ thus makes it possible to calculate the scalar product which corresponds to the product of the vectorial part of the coefficient $\beta$ by the dipolar moment $\mu$ of the molecule.

In order to further illustrate the present invention and the advantages thereof, the following specific examples are given, it being understood that same are intended only as illustrative and in nowise limitative.

EXAMPLE 1

Synthesis of 1-(parafluorophenyl)-1,1-dimethyl-2-(para-N,N-dimethylaminophenyl)-2,2-dimethyldisilane

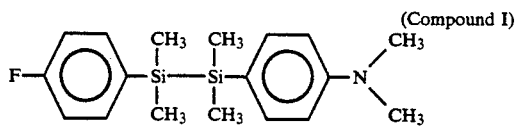
(Compound I)

First stage: Preparation of 1-(parafluorophenyl)-1,1-dimethyl-2,2-dimethyl-2-chlorodisilane First, parafluorobromobenzene magnesium was synthesized by reacting magnesium chips with parafluorobenzene in tetrahydrofuran as the solvent. This synthesis was carried out in a manner similar to the preparation of any magnesium derivative, under the same conditions.

The resulting magnesium compound was immediately reacted, while maintained in the tetrahydrofuran medium, with tetramethyldichlorodisilane. The exothermicity of the reaction was controlled by the rate of the addition of the magnesium compound to the solution of the tetramethyldichlorodisilane in the tetrahydrofuran.

After heating under reflux and elimination of the tetrahydrofuran under vacuum, the magnesium salts formed were eliminated by filtering the reaction medium dissolved in hexane under a nitrogen atmosphere.

The 1-(parafluorophenyl)-1,1-dimethyl-2-chlorodisilane was then recovered from the reaction medium by vacuum distillation.

The structure of the product obtained was confirmed by mass spectrography and NMR.

The amounts introduced were the stoichiometric amounts, or a slight excess thereof, in particular relative to the magnesium chips.

The weight yield of the reaction was on the order of 67%.

Second stage

The magnesium compound of parabromo-N,N-dimethylaniline was synthesized by the method of the first stage, in a tetrahydrofuran medium.

The magnesium compound obtained in this manner was added to a solution of 1-(parafluorophenyl)-1,1-dimethyl-2,2-dimethyl-2-chlorodisilane in tetrahydrofuran.

After filtering the magnesium salts formed, washing with water and drying the reaction medium, the 1-(parafluorophenyl)-1,1-dimethyl-2-(para-N,N-dimethylaminophenyl)-2,2-dimethyldisilane was crystallized in hexane and dried after filtration.

The amounts of the reagents used were the stoichiometric amounts.

The product obtained was a white solid in a purity higher than 95%, with a total yield of the synthesis of about The melting point of the compound was 52° C.

Analysis by IR, UV spectrometry, mass spectrometry or NMR confirmed the structure of the compound.

EXAMPLE 2

Preparation of paracarboxyphenyl-para-N,N-dimethylaminophenyl-methylphenylsilane

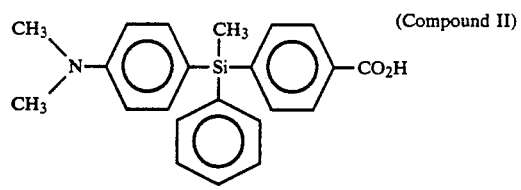
(Compound II)

This compound was synthesized utilizing a technique similar to that of Example 1; however, the respective starting materials were paradibromobenzene, methylphenyldichlorosilane and parabromo-N,N-dimethylaniline.

The product obtained, separated from the reaction medium by vacuum distillation, was a viscous orange oil, the IR, UV spectrometry, mass spectrometry and NMR analyses of which confirmed that it had the following formula:

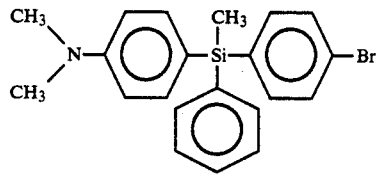

To synthesize Compound II, the above compound was carboxylated in a tetrahydrofuran reaction medium, by the formation of a magnesium compound by reaction with magnesium chips, then, after heating the reaction medium to reflux for 3 hours, carbon dioxide was bubbled through the reaction medium for 1 hour, 30 min, cooled to ambient temperature.

The reaction medium was then heated to reflux for 1 hour, then hydrolyzed by the addition of acidified water.

Compound II was extracted from the reaction medium by washing with either in an acid medium.

The ether was then evaporated. The resulting oil was dissolved hot in hexane. After cooling, Compound II crystallized in the form of a solid yellow scale, having a melting point of 80° C., with a weight yield of the synthesis of 30%.

IR, UV and mass spectrometry and NRM analysis confirmed the structure of Compound II.

EXAMPLES 3 TO 13

The compounds of Table I were prepared by the processes described in Examples 1 or 2. This Table also indicates the starting materials used and the properties of the final products.

In these examples, an organosilicon compound was first synthesized containing one or more electron donating groups $R_1$, by magnesium synthesis. Secondly, the electron accepting groups $R_2$ were obtained by the conversion of a substituent of an aryl radical attached to the organosilicon molecule by magnesium synthesis.

Thus, to obtain the Compounds IV and V, the Knoevenagel reaction was applied to the organosilicon compound containing an aryl radical substituted by a formyl group (the latter being obtained by the action of dimethyl formamide on the corresponding organomagnesium) with the compound CN—CH₂—PO₃(C₂H₅)₂.

For the Compounds VI to IX and XII, the compound CN—CH₂—CN, and for the compounds X, XI and XIII, the compound NO₂—CH₂—CN, were reacted instead of the compound CN—CH₂—PO₃(C₂H₅)₂.

The structures of these compounds were confirmed by infrared and UV spectroscopy, by mass spectroscopy and by NMR analysis.

TABLE I

| Example | Compound | Formula | Nature | Starting Materials |
|---|---|---|---|---|
| 3 | III | CH₃O—C₆H₃(OCH₃)—Si(CH₃)₂—C₆H₄—F | oil | Br—C₆H₄—F; Cl—Si(CH₃)₂—Si(CH₃)₂—Cl; CH₃O—C₆H₃(OCH₃)—Br |
| 4 | IV | (CH₃)₂N—C₆H₄—Si(CH₃)₂—C₆H₄—CH=C(CN)—PO₃(C₂H₅)₂ | oil | (CH₃)₂N—C₆H₄—Br; Cl—Si(CH₃)₂—Cl; Br—C₆H₄—Br |
| 5 | V | (CH₃)₂N—C₆H₄—[Si(CH₃)₂]₂—C₆H₄—CH=C(CN)—PO₃(C₂H₅)₂ | oil | (CH₃)₂N—C₆H₄—Br; Cl—[Si(CH₃)₂]₂—Cl; Br—C₆H₄—Br |
| 6 | VI | (CH₃)₂N—C₆H₄—Si(CH₃)₂—C₆H₄—CH=C(CN)₂ | oil | (CH₃)₂N—C₆H₄—Br; Cl—Si(CH₃)₂—Cl; Br—C₆H₄—Br |
| 7 | VII | (CH₃)₂N—C₆H₄—[Si(CH₃)₂]₂—C₆H₄—CH=C(CN)₂ | solid | (CH₃)₂N—C₆H₄—Br; Cl—[Si(CH₃)₂]₂—Cl; Br—C₆H₄—Br |
| 8 | VIII | (CH₃)₂N—C₆H₄—Si(CH₃)(C₆H₄—N(CH₃)₂)—C₆H₄—CH=C(CN)₂ | solid | (CH₃)₂N—C₆H₄—Br; CH₃SiCl₃; Br—C₆H₄—Br |
| 9 | IX | (CH₃)₂N—C₆H₄—Si(CH₃)(C₆H₄—CH=C(CN)₂)—C₆H₄—CH=C(CN)₂ | solid | (CH₃)₂N—C₆H₄—Br; CH₃SiCl₃; Br—C₆H₄—Br |
| 10 | X | (CH₃)₂N—C₆H₄—Si(CH₃)₂—C₆H₄—CH=C(CN)(NO₂) | oil | (CH₃)₂N—C₆H₄—Br; Si(CH₃)₂Cl₂; Br—C₆H₄—Br |
| 11 | XI | (CH₃)₂N—C₆H₄—[Si(CH₃)₂]₂—C₆H₄—CH=C(CN)(NO₂) | solid | (CH₃)₂N—C₆H₄—Br; Cl—[Si(CH₃)₂]₂—Cl; Br—C₆H₄—Br |
| 12 | XII | (CH₃)₂N—C₆H₄—[Si(CH₃)₂]₆—C₆H₄—CH=C(CN)₂ | solid | (CH₃)₂N—C₆H₄—Br; Cl—[Si(CH₃)₂]₆—Cl; Br—C₆H₄—Br |

TABLE I-continued

| Example | Compound | Formula | Nature | Starting Materials |
|---|---|---|---|---|
| 13 | XIII |  | solid |  |

These molecules were tested in electrooptic devices and were found to be active in nonlinear optics.

The results of the determination of the hyperpolarizability coefficient $\beta$ for certain of these molecules are reported in Table II:

TABLE II

| Compounds | $\beta\mu$ in D.esu |
|---|---|
| I | $15.7 \times 10^{-30}$ |
| VI | $96 \times 10^{-30}$ |
| VII | $210 \times 10^{-30}$ |
| Urea | $2 \times 10^{-30}$ |

These measurements evidenced that the molecules synthesized have a non-zero hyperpolarizability coefficient $\beta$, which may be significantly superior to that of urea.

The compounds of the invention are used in components of electrooptic devices in the form of shaped articles, such as, for example, films, by incorporation into a material, such as a polymer, a resin, etc., by conventional and known techniques.

Thus, for example, the compounds prepared according to Examples 1 to 13 are incorporated into a transparent polymer film of a thickness of 10 to 200 μm, as described in EP 218,938. Suitable such polymers are, for example, polymethylmethacrylate, atactic polystyrene, and the like.

The polymer film is heated to a temperature higher than its glass transition temperature (Tg), then subjected to an intense electrical field to orient the active molecules according to the invention.

The film is then cooled to a temperature less than its glass transition temperature, Tg, in order to freeze the active molecules in their oriented position A film containing the oriented active molecules according to the invention has an electrooptic coefficient r and a second harmonic generation coefficient comparable, and even superior to those of the inorganic crystals usually employed for these applications, such as, for example, potassium diphthalate, ammonium diphthalate, lithium nitrate, etc.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An organosilicon compound having the following general formula:

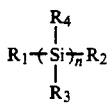

in which n is an integer ranging from 1 to 20; $R_1$ is a radical of the following general formula:

$$-R_5-D_m$$

in which $R_5$ is an arylene radical; the radicals D, which may be identical or different, are each a hydrogen atom or an electron donating group selected from among amino, alkylamino, dialkylamino, arylamino, hydroxyl, thiolo, alkylthio, arylthio, alkoxy, aryloxy, haloalkyl, oxy,

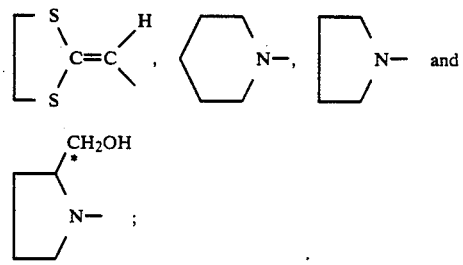

and m is an integer equal to 1, 2 or 3, with the proviso that D is not a hydrogen atom when $R_2$ is an aryl radical that is not substituted by one or more electron attracting groups; $R_2$ is a pyridinyloxy radical or a radical of the general formula:

$$-R_6-A_p$$

in which $R_6$ is an aryl radical; p is an integer equal to 1, 2 or 3; and the radicals A, which may be identical or different, are each a hydrogen atom or an electron accepting group selected from among halo, nitro, cyano, nitroso, quaternary ammonium, pyridinyloxy, $CF_3$, alkyl quaternary ammonium, acyl, alkoxysulfonyl, aryloxsulfonyl, radicals, or a radical of the following formulae:

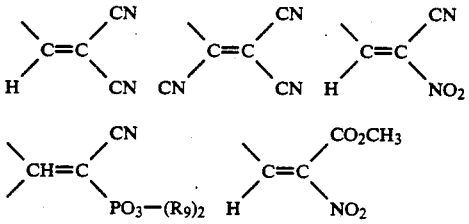

wherein $R_9$ is an alkyl radical having from 1 to 6 carbon atoms or an aryl radical, with the proviso that A is not a hydrogen atom when $R_1$ is an aryl radical that is not substituted by one or more electron donating groups; $R_3$ is an alkyl radical having from 1 to 8 carbon atoms, a hydrogen atom, an aryl radical, or an $R_1$ or $R_2$ radical; and $R_4$ is an alkyl radical having from 1 to 8 carbon atoms, a hydrogen atom, an aryl radical, or an $R_1$ radical when $R_3$ is not an $R_2$ radical or an $R_2$ radical when $R_3$ is not an $R_1$ radical.

2. The organosilicon compound as defined by claim 1, wherein $R_3$ and $R_4$ are each a radical $R_1$ or $R_2$, or are methyl, ethyl, propyl or phenyl radicals.

3. The organosilicon compound as defined in claim 2, wherein $R_1$ is one of the following radicals:

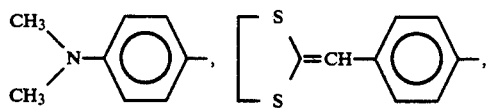

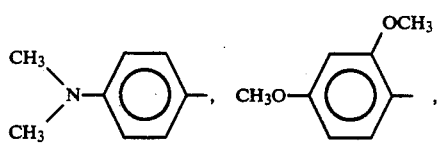

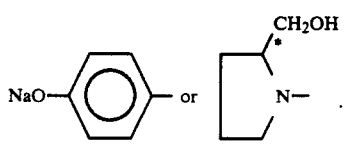

4. The organosilicon compound as defined by claim 2, wherein $R_2$ is one of the following radicals;

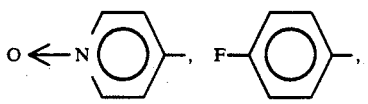

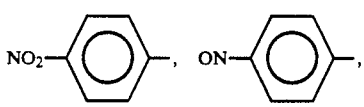

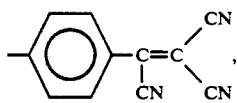

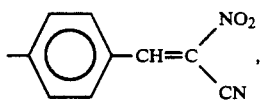

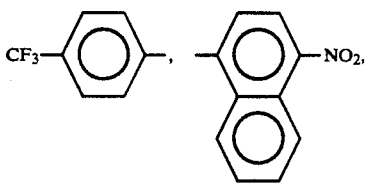

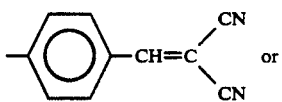

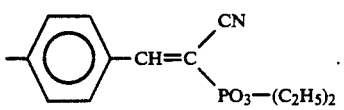

5. The organosilicon compound having one of the following formulae:

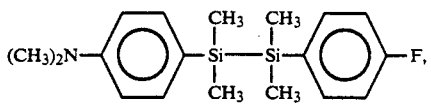

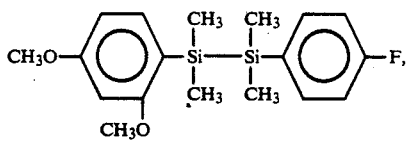

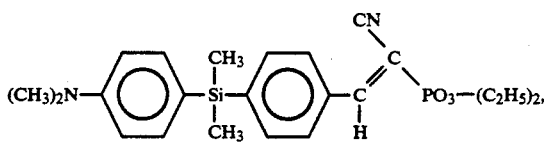

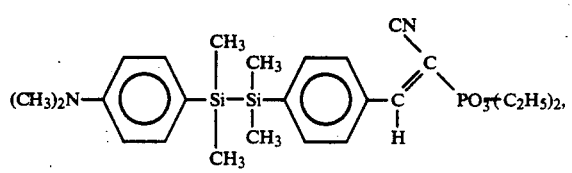

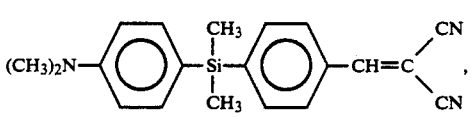

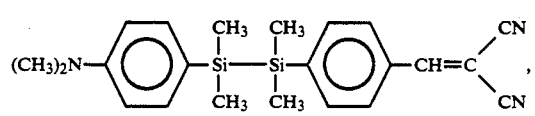

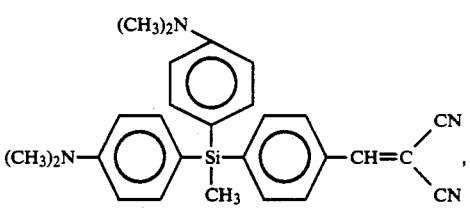

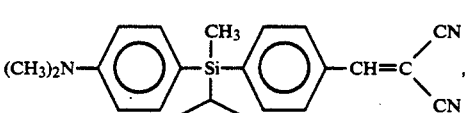

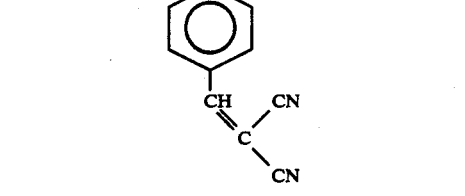

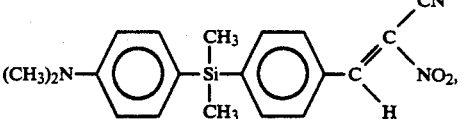

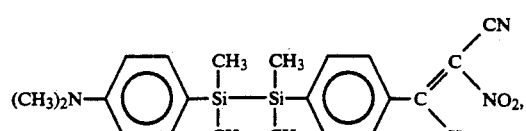

-continued

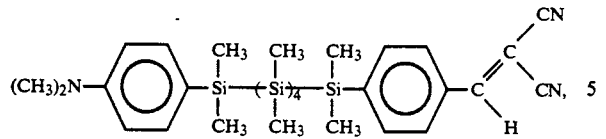

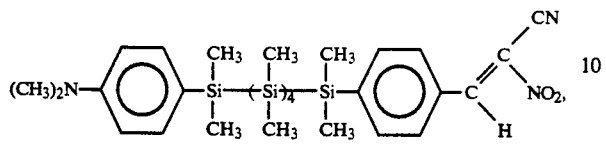

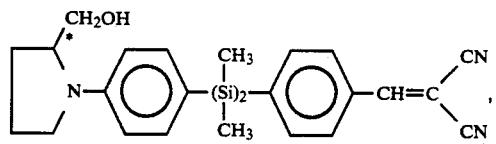

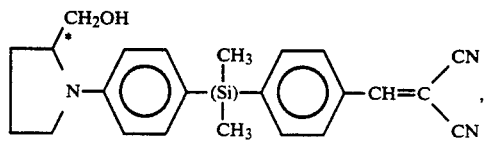

or

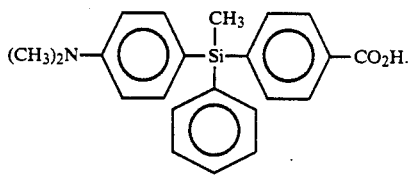

6. An organosilicon compound having the following general formula:

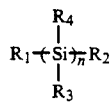

in which n is an integer ranging from 1 to 20; $R_1$ is an electron donating group; $R_2$ is an electron accepting group; $R_3$ is an alkyl radical having from 1 to 8 carbon atoms, a hydrogen atom, an aryl radical, or an $R_1$ or $R_2$ radical; and $R_4$ is an alkyl radical having from 1 to 8 carbon atoms, a hydrogen atom, an aryl radical, or an $R_1$ radical when $R_3$ is not an $R_2$ radical or an $R_2$ radical when $R_3$ is not an $R_1$ radical; said compound having a second order hyperpolarizability coefficient greater than zero.

7. The organosilicon compound as defined by claim 6, having a hyperpolarizability coefficient $\beta$ greater than the coefficient $\beta$ of urea.

8. The organosilicon compound as defined by claim 7, having a hyperpolarizability coefficient $\beta$ of at least about 7 times greater than the coefficient $\beta$ of urea.

9. A process for the preparation of an organosilicon compound having the following general formula:

in which n is an integer ranging from 1 to 20; $R_1$ is an electron donating group; $R_2$ is an electron accepting group; $R_3$ is an alkyl radical having from 1 to 8 carbon atoms, a hydrogen atom, an aryl radical, or an $R_1$ or $R_2$ radical; and $R_4$ is an alkyl radical having from 1 to 8 carbon atoms, a hydrogen atom, an aryl radical, or an $R_1$ radical when $R_3$ is not an $R_2$ radical or an $R_2$ radical when $R_3$ is not an $R_1$ radical, comprising (a) reacting a magnesium derivative of the compound $R_1$—X, wherein X is a halogen, with a halosilane of the formula:

wherein each X is also a halogen, and $R_7$ and $R_8$, which may be identical or different, are each $R_1$, $R_2$, $R_3$ or $R_4$, and then (b) reacting the product of reaction of step (1) with a magnesium derivative of the compound $R_2$—X, wherein X is also a halogen.

* * * * *